(12) United States Patent
Wei et al.

(10) Patent No.: US 9,567,298 B2
(45) Date of Patent: Feb. 14, 2017

(54) CRYSTAL FORMS OF AZETIDINONE COMPOUNDS AND PREPARING METHODS THEREOF

(71) Applicant: Zhejiang Hisun Pharmaceutical Co., Ltd., Taizhou (CN)

(72) Inventors: Hongyuan Wei, Tianjin (CN); Chongjun Liu, Tianjin (CN); Xuyang Zhao, Chengdu (CN); Xiaojie Xu, Taizhou (CN); Hua Bai, Taizhou (CN); Yuncai Zhang, Taizhou (CN)

(73) Assignee: Zhejiang Hisun Pharmaceutical Co., Ltd. (CN)

( * ) Notice: Subject to any disclaimer, the term of this patent is extended or adjusted under 35 U.S.C. 154(b) by 0 days.

(21) Appl. No.: 14/426,085

(22) PCT Filed: Sep. 5, 2013

(86) PCT No.: PCT/CN2013/082998
§ 371 (c)(1),
(2) Date: Mar. 4, 2015

(87) PCT Pub. No.: WO2014/036956
PCT Pub. Date: Mar. 13, 2014

(65) Prior Publication Data
US 2015/0218091 A1  Aug. 6, 2015

(30) Foreign Application Priority Data

Sep. 5, 2012  (CN) .......................... 2012 1 0323683

(51) Int. Cl.
*C07D 205/08* (2006.01)
*A61K 31/397* (2006.01)
(52) U.S. Cl.
CPC .......... *C07D 205/08* (2013.01); *A61K 31/397* (2013.01)
(58) Field of Classification Search
None
See application file for complete search history.

(56) References Cited

U.S. PATENT DOCUMENTS 8,623,855 B2  1/2014 Bai et al.

FOREIGN PATENT DOCUMENTS

| | | | |
|---|---|---|---|
| CN | CA 2770793 A1 * | 2/2011 | .......... A61K 31/397 |
| WO | 2011017907 A1 | 2/2011 | |

OTHER PUBLICATIONS

International Search Report for Application No. PCT/CN2013/082998 dated Dec. 12, 2013.

* cited by examiner

*Primary Examiner* — Golam M M Shameem
*Assistant Examiner* — Laura Daniel
(74) *Attorney, Agent, or Firm* — Lerner, David, Littenberg, Krumholz & Mentlik, LLP

(57) ABSTRACT

The present invention provides crystal forms of the compound of (3R,4S)-4-(4-hydroxyphenyl)-3-[3-(4-fluorophenyl)-4-hydroxybut-2(Z)-enyl]-1-(4-fluorophenyl)-2-azetidinone (formula A). The crystal forms can be characterized by X-ray powder diffraction (XRPD) spectra, differential scanning calorimetry (DSC) spectra, infrared absorption spectra and so on. Meanwhile, the present invention also provides methods for preparing the crystal forms of the compound of formula A, pharmaceutical compositions and uses thereof.

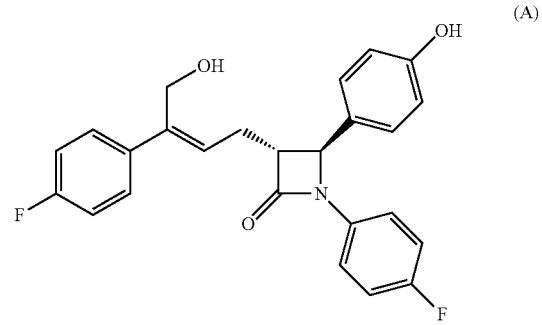

(A)

13 Claims, 8 Drawing Sheets

CRYSTAL FORMS OF AZETIDINONE COMPOUNDS AND PREPARING METHODS THEREOF

CROSS-REFERENCE TO RELATED APPLICATIONS

The present application is a national phase entry under 35 U.S.C. §371 of International Application No. PCT/CN2013/082998, filed on Sep. 5, 2013, published in Chinese, which claims priority from Chinese Patent Application No. 201210323683.5, filed Sep. 5, 2012, all of which are incorporated herein by reference.

FIELD OF THE INVENTION

The present invention belongs to the field of chemistry, and more specifically, the present invention relates to new crystal forms of (3R,4S)-4-(4-hydroxyphenyl)-3-[3-(4-fluorophenyl)-4-hydroxybut-2(Z)-enyl]-1-(4-fluorophenyl)-2-azetidinone and preparation methods thereof.

BACKGROUND OF THE INVENTION

A compound of azetidinone has a structure of formula A as follows and a chemical name of (3R,4S)-4-(4-hydroxyphenyl)-3-[3-(4-fluorophenyl)-4-hydroxybut-2(Z)-enyl]-1-(4-fluorophenyl)-2-azetidinone. The compound of formula A is a novel plasma cholesterol reducing agent, which is used for reducing plasma cholesterol contents, thus being used for treating diseases highly correlated to the plasma cholesterol contents. WO2011017907 discloses a compound of formula A and preparation methods and applications thereof.

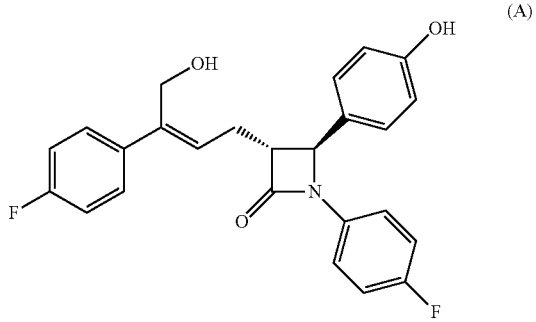 [SMILES: O=C1[C@H](C/C=C(\CO)c2ccc(F)cc2)[C@@H](c2ccc(O)cc2)N1c1ccc(F)cc1]

(A)

No report about the crystal forms of the compound of formula A is found at present. The inventor obtains the crystal forms of the compound of formula A through conducting a large number of experiments.

BRIEF SUMMARY OF THE INVENTION

Therefore, the object of the present invention is to provide crystal forms of the compound of (3R,4S)-4-(4-hydroxyphenyl)-3-[3-(4-fluorophenyl)-4-hydroxybut-2(Z)-enyl]-1-(4-fluorophenyl)-2-azetidinone of formula A structured as follows and the preparation methods thereof.

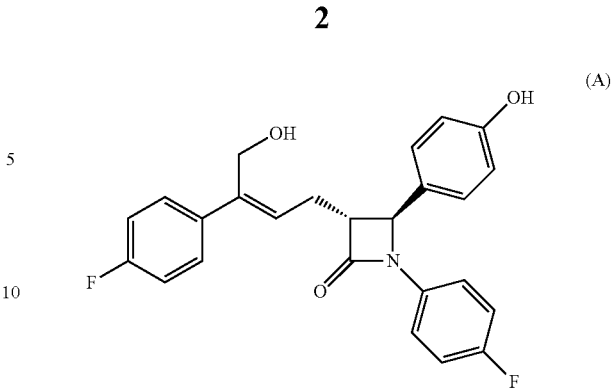

(A)

According to the object of the present invention, the present invention provides a crystal form I of the compound of formula A (hereinafter referred to as "crystal form I").

An X-ray powder diffraction (XRPD) spectrum of the crystal form I radiated by Cu-Kα and characterized in degrees 2θ has following characteristic peaks at 8.17±0.20°, 13.53±0.20°, 16.67±0.20°, 18.13±0.20°, 19.14±0.20°, 19.57±0.20°, 20.26±0.20°, 22.32±0.20°, 23.05±0.20°, 23.77±0.20°, 25.03±0.20°, 27.69±0.20° and 30.99±0.20°.

Preferably, the X-ray powder diffraction spectrum of the crystal form I characterized in degrees 2θ further has following characteristic peaks at 15.76±0.20°, 16.25±0.20°, 17.14±0.20°, 21.12±0.20°, 25.50+0.20°, 26.02±0.20°, 28.95±0.20°, 29.84±0.20°, 33.34±0.20°, 36.32±0.20° and 37.57±0.20°.

More preferably, the X-ray powder diffraction spectrum of the crystal form I characterized in degrees 2θ has following characteristic peaks and relative intensity at:

| Diffraction angle 2θ | Relative intensity % |
| --- | --- |
| 8.17 ± 0.20° | 10 |
| 13.53 ± 0.20° | 13 |
| 15.76 ± 0.20° | 3 |
| 16.25 ± 0.20° | 6 |
| 16.67 ± 0.20° | 11 |
| 17.14 ± 0.20° | 3 |
| 18.13 ± 0.20° | 38 |
| 19.14 ± 0.20° | 47 |
| 19.57 ± 0.20° | 14 |
| 20.26 ± 0.20° | 71 |
| 21.12 ± 0.20° | 3 |
| 22.32 ± 0.20° | 33 |
| 23.05 ± 0.20° | 100 |
| 23.77 ± 0.20° | 21 |
| 25.03 ± 0.20° | 13 |
| 25.50 ± 0.20° | 7 |
| 26.02 ± 0.20° | 4 |
| 27.69 ± 0.20° | 21 |
| 28.95 ± 0.20° | 4 |
| 29.84 ± 0.20° | 6 |
| 30.99 ± 0.20° | 9 |
| 33.34 ± 0.20° | 5 |
| 36.32 ± 0.20° | 3 |
| 37.57 ± 0.20° | 4 |

More preferably, the XRPD spectrum of the crystal form I is shown in FIG. 1.

Further, the differential scanning calorimetry (DSC) spectrum of the crystal form I is shown in FIG. 2.

Further, the infrared (IR) spectrum of the crystal form I is shown in FIG. 3.

The infrared absorption peak and relative absorption intensity data of the crystal form I are shown as follows.

| Infrared absorption wave number (cm$^{-1}$) | Relative absorption |
|---|---|
| 430.1189 | 0.86744 |
| 514.9855 | 0.46846 |
| 636.4989 | 0.86912 |
| 721.3654 | 0.85935 |
| 783.0865 | 0.49801 |
| 827.4485 | 0.12002 |
| 898.8136 | 0.91525 |
| 941.2468 | 0.81022 |
| 1010.683 | 0.29323 |
| 1105.194 | 0.51903 |
| 1157.271 | 0.4074 |
| 1222.849 | 0.11491 |
| 1355.935 | 0.36791 |
| 1392.582 | 0.2545 |
| 1440.802 | 0.64795 |
| 1508.309 | 0.01676 |
| 1602.82 | 0.50812 |
| 1724.333 | 0.02433 |
| 1888.28 | 0.86998 |
| 2821.812 | 0.94387 |
| 2883.533 | 0.86289 |
| 2945.254 | 0.90718 |
| 3032.049 | 0.8926 |
| 3381.159 | 0.4183 |

According to the object of the present invention, the present invention provides the preparation methods of the crystal form I. The preparation method for obtaining the crystal form I can be selected from any one of the following methods.

Method (1), comprising the following steps of:

1) dissolving the compound of formula A into an organic solvent to prepare a saturated solution, wherein the organic solvent is selected from $C_1$-$C_4$ linear alcohol, acetonitrile, furans, carboxylic acid, ester, amide or ketone;

2) adding water or $C_2$-$C_8$ ether anti-solvent more than one time of the volume of the organic solvent in step 1) into the foregoing saturated solution all in once to crystallize out the solids of the crystal form I; and 3) collecting the obtained solids, thus obtaining the crystals in form I.

In step 1) of the method (1), the carboxylic acid is preferably $C_{1-6}$ carboxylic acid, the ester is preferably $C_{1-6}$ alkyl $C_{1-6}$ carboxylate, the amide is preferably N—$C_{1-6}$ alkylamide or N,N-bi-$C_{1-6}$ alkylamide, and the ketone is preferably $C_{3-6}$ ketone.

In a further embodiment, the organic solvent in step 1) of the method (1) is selected from methanol, ethanol, n-propanol, iso-propanol, n-butylalcohol, tetrahydrofuran, acetic acid, ethyl acetate, acetonitrile, N,N-dimethylformamide or acetone; and is more preferably methanol or ethanol.

The volume of the water or $C_2$-$C_8$ ether anti-solvent added in step 2) of the method (1) is 1-10 times of the volume of the organic solvent, and is preferably 1.5 times. Further preferably, the anti-solvent is water.

In a further embodiment, the preparation method (1) of the crystal form I comprises the following steps of: dissolving one portion of the compound of formula A in g into one portion of methanol in mL to prepare a saturated solution thereof under the normal temperature, then adding 10 portions of anti-solvent water in mL into the foregoing saturated solution all at once, immediately filtrating solids that are crystallized out, placing the solids in a vacuum drying oven for drying, wherein the dried solids are namely the crystal form I.

Method (2), comprising the following steps of:

1) dissolving the compound of formula A into $C_{1-6}$ alkyl $C_{1-6}$ carboxylate to obtain a solution, wherein the ratio of the mass of the compound of formula A in g to the volume of the $C_{1-6}$ alkyl $C_{1-6}$ carboxylate in mL is 1:1.5-5;

2) adding $C_6$-$C_7$ alkane anti-solvent dropwise 1-3 times of the volume of the $C_{1-6}$ alkyl $C_{1-6}$ carboxylate in step 1) into the foregoing solution to crystallized out the solids in the crystal form I; and 3) collecting the obtained solids, thus obtaining the crystals in form I.

In step 1) of the method (2), the $C_{1-6}$ alkyl $C_{1-6}$ carboxylate is preferably ethyl acetate.

In step 2) of the method (2), the $C_6$-$C_7$ alkane is preferably n-hexane or n-heptane.

In a further embodiment, the preparation method (2) of the crystal form I comprises the following steps of: adding one portion of the compound of formula A in g into a crystallizer (for example, 10 times of the volume), adding two portions of ethyl acetate in mL thereinto, stirring at the room temperature till complete dissolving to obtain a solution, adding two portions of n-heptane in mL dropwise into the foregoing solution to crystallize a large amount of solids, then performing vacuum drying on the solids after the solids are filtrated out, wherein the dried solids are namely the crystal form I.

Method (3), comprising the following steps of:

adding one portion of the compound of formula A in g into five portions of methylene chloride in mL, completely dissolving under heating and refluxing conditions, then slowly cooling to the normal temperature, separating out solids, filtrating, and drying at the normal temperature and the normal pressure, wherein the dried solids are namely the crystal form I.

Method (4), comprising the following steps of:

adding one portion of the compound of formula A in g into 10 portions of toluene in mL, completely dissolving under heating and refluxing conditions, then slowly cooling to the normal temperature, crystallizing out solids, filtrating, and drying at the normal temperature and the normal pressure, wherein the dried solids are namely the crystal form I.

According to the object of the present invention, the present invention provides a crystal form II of the compound of formula A (hereinafter referred to as "crystal form II").

An X-ray powder diffraction spectrum of the crystal form II radiated by Cu-Kα and characterized in degrees 2θ has following characteristic peaks at 5.20±0.20°, 7.46±0.20°, 8.70±0.20°, 10.60±0.20°, 11.84±0.20°, 17.14±0.20°, 20.36±0.20° and 26.48±0.20°.

Preferably, the X-ray powder diffraction spectrum of the crystal form II characterized in degrees 2θ further has following characteristic peaks at 6.29±0.20°, 6.96±0.20°, 12.82±0.20°, 13.28±0.20°, 14.21±0.20°, 15.02±0.20°, 15.40±0.20°, 16.40±0.20°, 17.61±0.20°, 18.34±0.20°, 18.62±0.20°, 19.06±0.20°, 19.58±0.20°, 20.02±0.20°, 21.50±0.20°, 22.18±0.20°, 22.74±0.20°, 23.41±0.20, 24.06±0.20°, 24.34±0.20°, 24.70±0.20°, 25.16±0.20°, 27.34±0.20°, 28.00±0.20°, 28.88±0.20°, 29.36±0.20°, 31.39±0.20°, 32.02±0.20°, 32.60±0.20° and 34.42±0.20°.

More preferably, the X-ray powder diffraction spectrum of the crystal form II characterized in degrees 2θ has following characteristic peaks and relative intensity at:

| Diffraction angle 2θ | Relative intensity % |
|---|---|
| 5.20 ± 0.20° | 39 |
| 6.29 ± 0.20° | 4 |
| 6.96 ± 0.20° | 29 |
| 7.46 ± 0.20° | 84 |

-continued

| Diffraction angle 2θ | Relative intensity % |
|---|---|
| 8.70 ± 0.20° | 28 |
| 10.60 ± 0.20° | 18 |
| 11.84 ± 0.20° | 27 |
| 12.82 ± 0.20° | 3 |
| 13.28 ± 0.20° | 3 |
| 14.21 ± 0.20° | 4 |
| 15.02 ± 0.20° | 13 |
| 15.40 ± 0.20° | 7 |
| 16.40 ± 0.20° | 33 |
| 17.14 ± 0.20° | 25 |
| 17.61 ± 0.20° | 13 |
| 18.34 ± 0.20° | 28 |
| 18.62 ± 0.20° | 33 |
| 19.06 ± 0.20° | 11 |
| 19.58 ± 0.20° | 17 |
| 20.02 ± 0.20° | 23 |
| 20.36 ± 0.20° | 28 |
| 21.50 ± 0.20° | 100 |
| 22.18 ± 0.20° | 17 |
| 22.74 ± 0.20° | 20 |
| 23.41 ± 0.20° | 6 |
| 24.06 ± 0.20° | 13 |
| 24.34 ± 0.20° | 11 |
| 24.70 ± 0.20° | 12 |
| 25.16 ± 0.20° | 23 |
| 26.48 ± 0.20° | 16 |
| 27.34 ± 0.20° | 6 |
| 28.00 ± 0.20° | 11 |
| 28.88 ± 0.20° | 11 |
| 29.36 ± 0.20° | 4 |
| 31.39 ± 0.20° | 5 |
| 32.02 ± 0.20° | 4 |
| 32.60 ± 0.20° | 3 |
| 34.42 ± 0.20° | 3 |

More preferably, the XRPD spectrum of the crystal form II is shown in FIG. 4.

Further, the differential scanning calorimetry (DSC) spectrum of the crystal form II is shown in FIG. 5.

Further, the infrared (IR) spectrum of the crystal form II is shown in FIG. 6.

The infrared absorption peak and relative absorption intensity data of the crystal form II are shown as follows.

| Infrared absorption wave number (cm$^{-1}$) | Relative absorption |
|---|---|
| 430.1189 | 0.9543 |
| 520.7718 | 0.69298 |
| 628.7837 | 0.91287 |
| 734.8669 | 0.82243 |
| 827.4485 | 0.46604 |
| 879.5257 | 0.95653 |
| 948.962 | 0.91914 |
| 1012.612 | 0.67808 |
| 1101.336 | 0.74233 |
| 1155.342 | 0.66551 |
| 1224.778 | 0.38758 |
| 1354.007 | 0.69178 |
| 1390.654 | 0.5504 |
| 1444.66 | 0.76162 |
| 1510.238 | 0.12598 |
| 1604.749 | 0.72333 |
| 1726.262 | 0.23374 |
| 1888.28 | 0.9551 |
| 2684.868 | 0.967 |
| 2819.883 | 0.94866 |
| 2902.821 | 0.89406 |
| 2966.471 | 0.8802 |
| 3068.696 | 0.89403 |
| 3240.358 | 0.81058 |
| 3379.23 | 0.75873 |
| 3489.171 | 0.73966 |

According to the object of the present invention, the present invention provides a preparation method of the crystal form II. The preparation method comprises the following steps of:

1) adding the compound of formula A into $C_1$-$C_3$ alcohol, optionally heating to dissolve the compound and obtain a solution, wherein the ratio of the mass of the compound of formula A in g to the volume of the $C_1$-$C_3$ alcohol in mL is 1:2-10;

2) adding water into the foregoing solution and ensuring that no crystal is crystallized out; and 3) naturally volatilizing the solvent at the normal temperature and the normal pressure, and collecting solids that are crystallized out, thus obtaining the crystals in form II.

Preferably, the $C_1$-$C_3$ alcohol in step 1) is ethanol or iso-propanol.

Preferably, the ratio of the volume of the water added in step 2) to the volume of the $C_1$-$C_3$ alcohol is 10:1-6, and is more preferably 10:2.

Preferably, the ratio of the mass of the compound of formula A in g to the volume of the $C_1$-$C_3$ alcohol in mL in step 1) is 1:2-5.

In a further embodiment, the preparation method of the crystal form II comprises the following steps of: adding 0.7 portion of the compound of formula A in g into a crystallizer (e.g., 18 times of volume), then adding 1.7 portions of ethanol in mL thereinto, heating to 50° C. for complete dissolving, then adding one portion of water (e.g., purified water) in mL thereinto, stopping heating, cooling naturally, volatilizing the solvent at the normal temperature and pressure, crystallizing out crystals (acicular), filtering, and drying (for example, 24 h) the crystals at the normal temperature to obtain the crystals in form II.

According to the object of the present invention, the present invention provides a crystal form III of the compound of formula A (hereinafter referred to as "crystal form III").

An X-ray powder diffraction spectrum of the crystal form III radiated by Cu-Kα and characterized in degrees 2θ has following characteristic peaks at: 8.16±0.20°, 12.02±0.20°, 14.38±0.20°, 17.60±0.20°, 18.36±0.20° and 20.98±0.20°.

Preferably, the X-ray powder diffraction spectrum of the crystal form III characterized in degrees 2θ further has following characteristic peaks at 6.06±0.20°, 8.74±0.20°, 10.32±0.20°, 13.22±0.20°, 14.78±0.20°, 15.36±0.20°, 16.12±0.20°, 16.52±0.20°, 17.08±0.20°, 18.70±0.20°, 19.04±0.20°, 20.06±0.20°, 21.52±0.20°, 22.36±0.20°, 22.84±0.20°, 23.50±0.20°, 24.20±0.20°, 24.84±0.20°, 25.10±0.20°, 26.18±0.20°, 26.66±0.20°, 27.12±0.20°, 27.44±0.20°, 28.44±0.20°, 29.02±0.20°, 29.62±0.20°, 30.62±0.20°, 31.16±0.20°, 31.58±0.20°, 33.47±0.20° and 33.73±0.20°.

More preferably, the X-ray powder diffraction spectrum of the crystal form III characterized in the degrees 2θ has following characteristic peaks and relative intensity at:

| Diffraction angle 2θ | Relative intensity % |
|---|---|
| 6.06 ± 0.20° | 4 |
| 8.16 ± 0.20° | 53 |
| 8.74 ± 0.20° | 9 |
| 10.32 ± 0.20° | 8 |
| 12.02 ± 0.20° | 37 |
| 13.22 ± 0.20° | 13 |
| 14.38 ± 0.20° | 34 |
| 14.78 ± 0.20° | 19 |
| 15.36 ± 0.20° | 34 |

-continued

| Diffraction angle 2θ | Relative intensity % |
|---|---|
| 16.12 ± 0.20° | 11 |
| 16.52 ± 0.20° | 40 |
| 17.08 ± 0.20° | 38 |
| 17.60 ± 0.20° | 94 |
| 18.36 ± 0.20° | 65 |
| 18.70 ± 0.20° | 100 |
| 19.04 ± 0.20° | 37 |
| 20.06 ± 0.20° | 91 |
| 20.98 ± 0.20° | 42 |
| 21.52 ± 0.20° | 34 |
| 22.36 ± 0.20° | 28 |
| 22.84 ± 0.20° | 31 |
| 23.50 ± 0.20° | 13 |
| 24.20 ± 0.20° | 24 |
| 24.84 ± 0.20° | 19 |
| 25.10 ± 0.20° | 41 |
| 26.18 ± 0.20° | 8 |
| 26.64 ± 0.20° | 12 |
| 27.12 ± 0.20° | 11 |
| 27.44 ± 0.20° | 13 |
| 28.44 ± 0.20° | 8 |
| 29.02 ± 0.20° | 9 |
| 29.62 ± 0.20° | 6 |
| 30.62 ± 0.20° | 5 |
| 31.16 ± 0.20° | 6 |
| 31.58 ± 0.20° | 6 |
| 33.47 ± 0.20° | 4 |
| 33.73 ± 0.20° | 4 |

More preferably, the XRPD spectrum of the crystal form III is shown in FIG. 7.

Further, the differential scanning calorimetry (DSC) spectrum of the crystal form III is shown in FIG. 8.

Further, the infrared (IR) spectrum of the crystal form III is shown in FIG. 9.

The infrared absorption peak and relative absorption intensity data of the crystal form III are shown as follows.

| Infrared absorption wave number (cm$^{-1}$) | Relative absorption |
|---|---|
| 426.2614 | 0.88521 |
| 524.6294 | 0.69233 |
| 609.4959 | 0.89427 |
| 736.7957 | 0.87285 |
| 825.5198 | 0.24393 |
| 920.0302 | 0.63294 |
| 1012.612 | 0.38132 |
| 1095.55 | 0.70228 |
| 1163.057 | 0.45052 |
| 1220.921 | 0.2604 |
| 1379.081 | 0.32645 |
| 1460.09 | 0.63607 |
| 1512.167 | 0.02957 |
| 1608.606 | 0.63564 |
| 1728.191 | 0.26212 |
| 1888.28 | 0.91463 |
| 2609.645 | 0.92228 |
| 2696.441 | 0.91122 |
| 2817.954 | 0.88812 |
| 2922.108 | 0.70643 |
| 2968.399 | 0.43922 |
| 3066.767 | 0.7935 |
| 3332.94 | 0.47441 |
| 3404.305 | 0.4607 |

According to the object of the present invention, the present invention provides a preparation method of the crystal form III. The preparation method comprises the following steps of:

1) adding the compound of formula A into a mixed solvent of $C_4$-$C_{10}$ alcohol and ethanol, optionally heating to dissolve the compound and obtain a solution, wherein the ratio of the volume of ethanol to the volume of $C_4$-$C_{10}$ alcohol is less than or equal to 0.2;

2) adding water more than one time of the volume of the foregoing mixed solvent into the foregoing solution; and 3) Crystallizing out the crystals, filtrating, and optionally drying to obtain the crystals in form III.

Preferably, the $C_4$-$C_{10}$ alcohol in step 1) is tert-butyl alcohol.

Preferably, the volume of the water added in step 2) is 2-10 times of the volume of the mixed solvent, and is preferably 2-3 times.

Preferably, the ratio of the mass of the compound of formula A in g to the volume of the $C_4$-$C_{10}$ alcohol in mL in step 1) is 1:8-15.

In a further embodiment, the preparation method of the crystal form III comprises the following steps of: adding 0.4 portion of the compound of formula A in g into a mixed solvent of four portions of tert-butyl alcohol and 0.3 portion of ethanol in mL, completely dissolving at the normal temperature to obtain a solution, adding 10 portions of water (for example, distilled water) in mL into the foregoing solution, crystallizing out the crystals, filtrating, and drying at the normal temperature and pressure to obtain the crystals in form III.

The present invention further provides another preparation method of the crystal form III, comprising the following steps of: adding one portion of the compound of formula A in g into a crystallizer (for example, 25 times of the volume), then adding 15 portions of tert-butyl alcohol in mL thereinto, dissolving sufficiently at 50° C., then naturally cooling to the room temperature to crystallizing out solids, filtrating the solid, and drying at the normal temperature and pressure, thus obtaining the crystals in form III.

In addition, the present invention further provides an amorphous form of the compound of formula A (hereinafter referred to as "amorphous form").

The amorphous form radiated by Cu-Kα has an X-ray powder diffraction spectrum as shown in FIG. 10.

Further, the DSC spectrum of the amorphous form is shown in FIG. 11.

Further, the IR spectrum of the amorphous form is shown in FIG. 12.

The infrared absorption peak and relative absorption intensity data of the amorphous form are shown as follows.

| Infrared absorption wave number (cm$^{-1}$) | Relative absorption |
|---|---|
| 426.2614 | 94% |
| 513.0567 | 68% |
| 543.9172 | 83% |
| 592.1368 | 92% |
| 619.1398 | 87% |
| 638.4277 | 89% |
| 704.0063 | 89% |
| 727.1517 | 87% |
| 781.1577 | 80% |
| 817.8046 | 47% |
| 833.2349 | 30% |
| 935.4605 | 89% |
| 991.3952 | 73% |
| 1012.612 | 59% |
| 1070.475 | 88% |
| 1103.265 | 69% |
| 1157.271 | 57% |
| 1224.778 | 32% |
| 1271.069 | 63% |
| 1355.935 | 66% |
| 1392.582 | 48% |

-continued

| Infrared absorption wave number (cm$^{-1}$) | Relative absorption |
|---|---|
| 1429.229 | 74% |
| 1450.446 | 67% |
| 1510.238 | 11% |
| 1598.962 | 59% |
| 1614.393 | 61% |
| 1722.405 | 23% |
| 1886.351 | 93% |
| 2858.459 | 91% |
| 2925.966 | 85% |
| 2956.827 | 86% |
| 3024.334 | 92% |
| 3078.34 | 91% |
| 3350.299 | 70% |
| 3367.658 | 70% |

According to the object of the present invention, the present invention provides a preparation method of the amorphous form. The preparation method comprises the following steps of:

1) dissolving the compound of formula A into an alcohol organic solvent to prepare a saturated solution;

2) adding alkane anti-solvent more than one time of the volume of the saturated solution into the foregoing saturated solution to form a slurry; and 3) lyophilizing the obtained slurry to obtain the solids in amorphous form.

Preferably, the alcohol organic solvent in step 1) is $C_1$-$C_{10}$ alcohol, and is more preferably $C_1$-$C_4$ alcohol, and is further preferably methanol or ethanol.

Preferably, the volume of the anti-solvent added in step 2) is 2-10 times of the volume of the saturated solution, and is more preferably 5 times.

Preferably, the alkane anti-solvent in step 2) is n-hexane or n-pentane.

In a further embodiment, the preparation method of the amorphous form comprises the following steps of: adding one portion of the compound of formula A in g into a crystallizer (for example, 18 times of the volume), then adding one portion of ethanol in mL thereinto, dissolving sufficiently at 50° C., then cooling to the room temperature, quickly adding five portions of n-hexane in mL thereinto under a quick stirring state to obtain a slurry (vaporous), lyophilizing (for example, one hour) the slurry to obtain the solids in amorphous form (white solid).

In this application, the steps of dissolving and crystal separating involved in all the above-mentioned methods generally require stirring unless otherwise noted. A known manner may be employed for stirring, for example, stirring via a magnetic force stirrer, mechanical stirring, and the like may be employed.

In this application, unless otherwise noted, the step of drying involved in all the above-mentioned methods may be carried out by employing a known manner, for example, vacuum drying, and the like. The drying temperature is generally 35-40° C. unless otherwise noted.

In this application, the normal temperature or the room temperature refers to 10-30° C., and is preferably 25° C.

In addition, the present invention provides a pharmaceutical composition/pharmaceutical preparation that comprises a therapeutically effective amount of the crystal form I or the crystal form II or the crystal form III. The pharmaceutical composition/pharmaceutical preparation includes but is not limited to general dosage form administration, for example, oral preparation form and injection preparation form, including capsule, tablet, powder, cachet, suspension and solution, wherein oral preparation form administration is preferable, and the tablet and capsule administration in the oral preparation form is more preferable.

In the pharmaceutical composition/pharmaceutical preparation, a pharmaceutically acceptable carrier or vehicle is further included. The pharmaceutically acceptable carrier or vehicle/additive includes but is not limited to avirulent compatible filler, adhesive, disintegrating agent, buffer, preservative, antioxidant, lubricant, corrigent, thickener, stain, emulsifying agent, and the like.

In addition, the present invention further provides an application of the crystal form I or the crystal form II or the crystal form III of the compound of formula A in preparing drugs for reducing plasma cholesterol contents.

The crystal form I or the crystal form II or the crystal form III of the compound of formula A according to the present invention may be used as a drug for reducing serum cholesterol. Therefore, the crystal form I or the crystal form II or the crystal form III of the compound of formula A according to the present invention can be used for treating or preventing such diseases as atherosclerosis and hypercholesterolemia, and the like.

In addition, the present invention further provides a method for reducing plasma cholesterol contents, which comprises the steps of giving the therapeutically effective amount of the crystal form I or the crystal form II or the crystal form III to a sufferer in need.

The compound of formula A according to the present invention can be prepared according to the process described in WO2011017907A1.

Advantages of the present invention: the present invention changes the solid-state physical properties of the drug compound of formula A through the foregoing manners. The solid-state physical properties comprise solid lapping liquidity, solid density, apparent crystal habit, solid melting point, and the like. These properties will affect the difficulty or facility of processing raw materials into drugs, the stability of the drugs during storage process, and the like. The drugs are easy to be processed into stable preparations to ensure the stability of the drugs only when the solid-state physical properties are well.

Another important solid-state property of drug compound is the dissolution rate of the drug compound in an aqueous fluid. The dissolution rate of active ingredients in the gastric juice of the sufferer has the result of therapeutics because the dissolution rate is the upper limit of the rate of the active ingredients of oral administration arriving at the blood. When preparing syrup, elixir and other liquid drugs, the dissolution rate is also a factor to be considered.

The molecular conformation and orientation of a unit cell may affect the foregoing actual physical properties. A specific heteromorphic form of a substance can be determined using the unit cell. The heteromorphic form enables the thermal behavior of the crystal to differ from amorphous substances or other heteromorphic forms.

The finding of the officinal new crystal forms of the compound provides a new opportunity for improving the behavior characteristics of drugs. It expands the range of materials that can be selected for designing by pharmaceutists, for example, a pharmaceutical preparation has a targeted release performance or other performance in need.

Compared with the amorphous form, the crystal form I or the crystal form II or the crystal form III of the compound of formula A according to the present invention have the advantages of high crystal form stability, high purity, and convenience for the storage and transportation. With regard to the handling process, the process of handling solids in the crystal forms can be safer as the hazard of dust explosion can be reduced; and the crystal form has better performances on pharmaceutics than that of the amorphous form.

DETAILED DESCRIPTION

The present invention will be further described hereinafter with references to the embodiments. It should be understood that the preparation methods according to the embodiments of the present invention are for explanation merely, but not to limit the present invention. Any simple improvement figured out on the preparation methods of the present invention under the concept of the present invention shall all fall within the protection scopes claimed by the present invention.

Instruments used for determining the XRPD, DSC and IR spectra of various new crystal forms and amorphous form of the present invention and the determining conditions are as follows.

Figure 4:
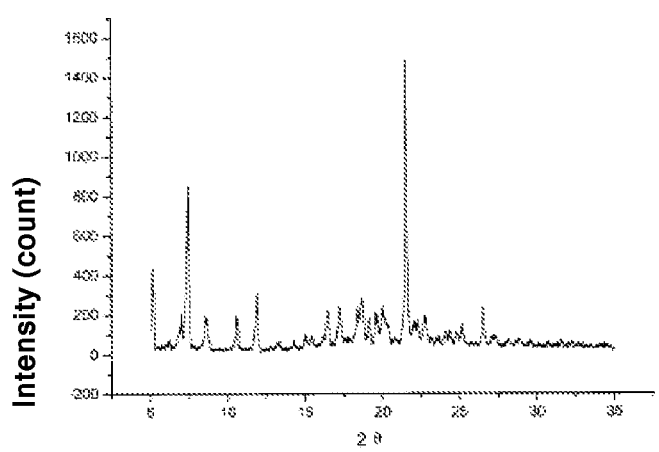
FIG. 4 is the XRPD spectrum of a crystal form II prepared in embodiment 9.
Figure 7:
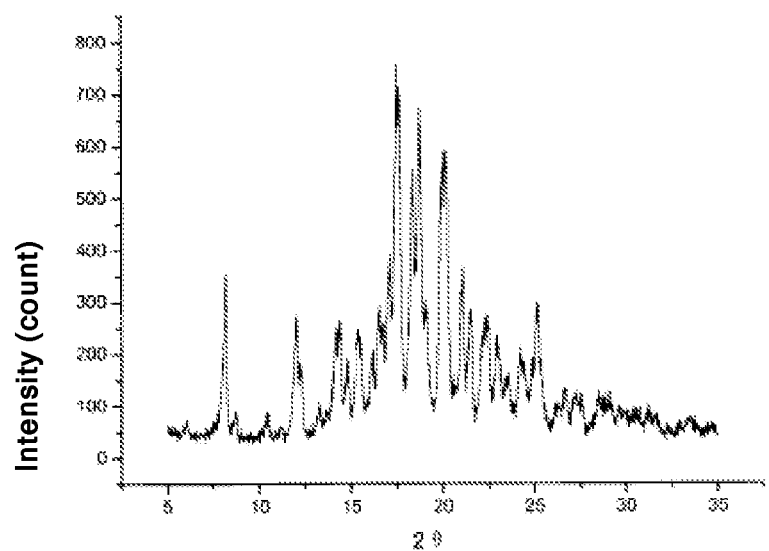
FIG. 7 is the XRPD spectrum of a crystal form III prepared in embodiment 13.
Figure 10:
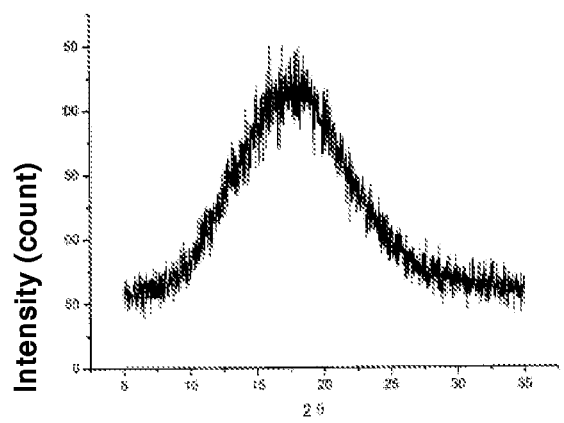
FIG. 10 is the XRPD spectrum of an amorphous form prepared in embodiment 16.

The instruments used for determining the XRPD spectra and the determining conditions are seen in Table 1 and Table 2. FIG. 4, FIG. 7 and FIG. 10 are obtained by using the instruments and determining conditions as shown in Table 1. FIG. 1, FIG. 13, FIG. 14 and FIG. 15 are obtained by using the instruments and determining conditions as shown in Table 2.

TABLE 1

Instruments used for determining XRPD spectra and determining conditions

| Model of instrument | Ri gaku D/max-2500 | Scanning range | 5°-50° (2θ) |
|---|---|---|---|
| Emitting target | Cu—Kα (1.5405 Å) | Scanning rate | 1step/s |
| Power supply settings | 40 kV, 100 mA | Scanning step | 0.02° |
| Receiving slit | 0.15 mm | Measuring temperature | (25 ± 1) ° C. |

TABLE 2

Instruments used for determining XRPD spectra and determining conditions

| Model of instrument | Ri gaku D/max-2200 | Scanning range | 3°-60° (2θ) |
|---|---|---|---|
| Emitting target | Cu—Kα (1.54056 Å) | Scanning rate | 3°/min |
| Power supply settings | 40 kV, 40 mA | Scanning step | 0.01° |
| Measuring temperature | (25 ± 1) ° C. | | |

Infrared (IR) spectral analysis: Bruker TENSOR 27 Fourier infrared spectrometer and DIGS detector are employed. The scanning range is 4000-400 cm$^{-1}$, and KBr tabletting method is adopted. 1.5 mg of samples is evenly mixed with 100 mg of KBr and pressed into sheets having a diameter of 13 mm, wherein the experimental data is collected and stored through an OPUS program.

DSC method: it is measured by employing the DSC1 of METTLER TOLEDO at a heating rate of 10° C./min. Specifically, DSC Mettler 1/700 differential scanning calorimeter is employed to analyze the samples. The weight of the samples ranges from 4 mg to 6 mg, the heating rate is 10° C./min, the protective gas is N2, and the flow rate of the protective gas is 120-150 mL/min.

Embodiment 1 preparation of (3R,4S)-4-(4-hydroxyphenyl)-3-[3-(4-fluorophenyl)-4-hydroxybut-2(Z)-enyl]-1-(4-fluorophenyl)-2-azetidinone (the compound of formula A)

Refer to the method of WO2011017907A1 for the preparation of the compound of formula A, wherein the details are as follows:

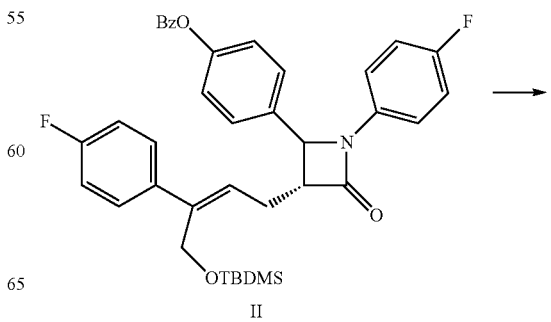

II

-continued

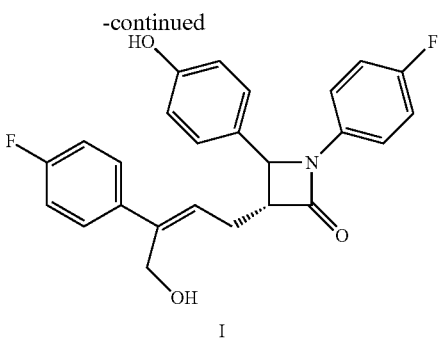

I

Step 1: add 32.5 mmol of compound II (formula Z), 250 mL of methanol, and 4.89 g (35.8 mmol) of potassium carbonate into a 500 mL reaction flask, and stir for 30 min at the room temperature. After the reaction is completed, extract for three times (300 mL×3) with ethyl acetate, combine organic phases, wash with a saturated saline solution, dry with anhydrous sodium sulfate, concentrate till it is dry, and keep stand-by.

Figure 15:
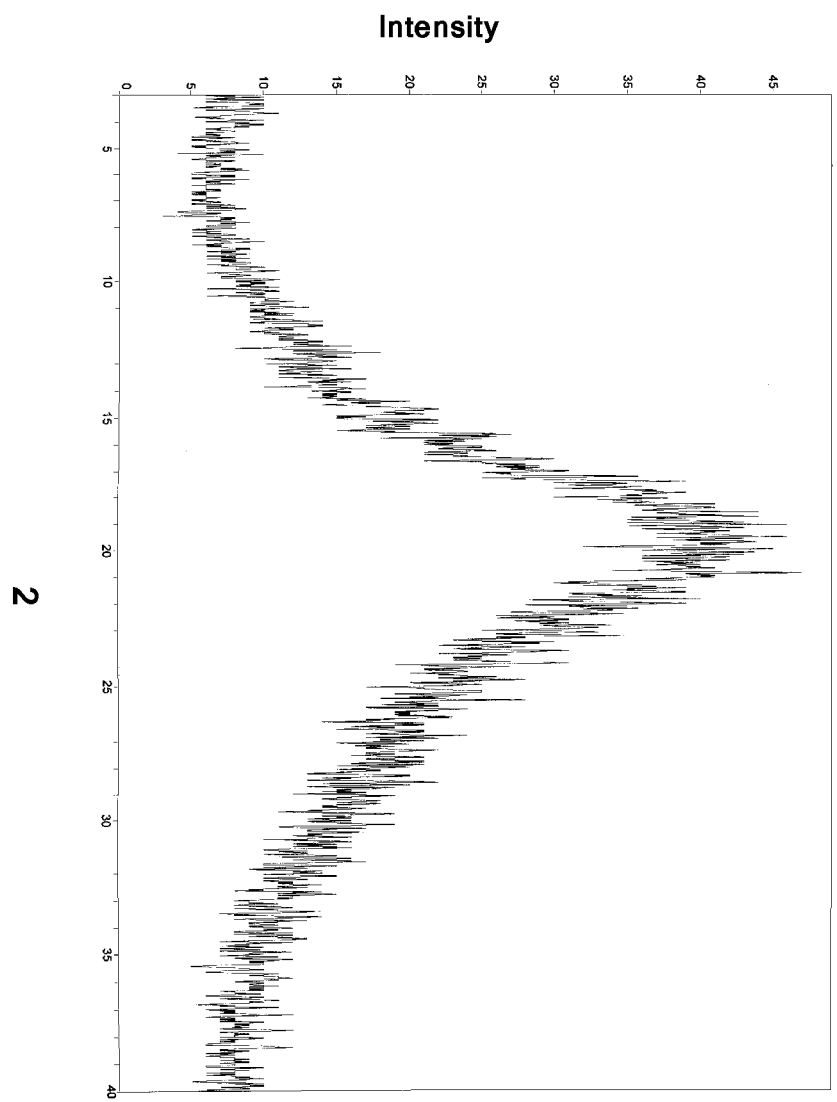
FIG. 15 is the XRPD spectrum of a compound of formula A prepared in embodiment 1.

Step 2: dissolve the product of step 1 with 200 mL of tetrahydrofuran, use 6 mol/L hydrochloric acid to adjust the pH at around 1, stir for 30 mins at the room temperature, then extract for three times (250 mL×3) with ethyl acetate, combine the organic phases, wash with a saturated with saline solution, dry with anhydrous sodium sulfate, concentrate till it is dry, use a solvent system of n-heptane and ethyl acetate (the volume ratio is 3:1) to carry out column chromatography separation, collect a target project, decompress, concentrate, and dry to obtain 8.14 g of the compound of formula A. The XRPD spectrum is shown in FIG. 15, indicating that it is an amorphous form.

1H NMR (400 MHz, DMSO-d6): δ2.72-2.84 (m, 2H, —CH2-), 3.20-3.25 (m, 1H, —CH—), 4.39 (d, 2H, J=5.2 Hz, —CH2-), 4.85 (t, 1H, J=5.2 Hz, —OH), 4.93 (d, 1H, J=2.3 Hz, —CH—), 5.80 (t, 1H, J=7.6 Hz, —CH—), 6.73-6.76 (m, 2H, Cpr-H), 7.10-7.20 (m, 4H, Cpr-H), 7.21-7.39 (m, 4H, Cpr-H), 8.40-7.42 (m, 2H, Cpr-H), 9.48 (s, 1H, —OH); MS (m/z): 422 [M+H].

Embodiment 2

Preparation of Crystal Form I

At the normal temperature, dissolve 1 g of the compound of formula A into 1 mL of methanol to prepare a saturated solution thereof, then add 10 mL of water into the saturated solution all at once, immediately filter out an obtained solid, place the solid into a vacuum drying oven for drying (the drying temperature is 35-40° C.), wherein the dried solids are namely the crystal form I. The output is 0.73 g, and the yield is 73%.

Figure 1:
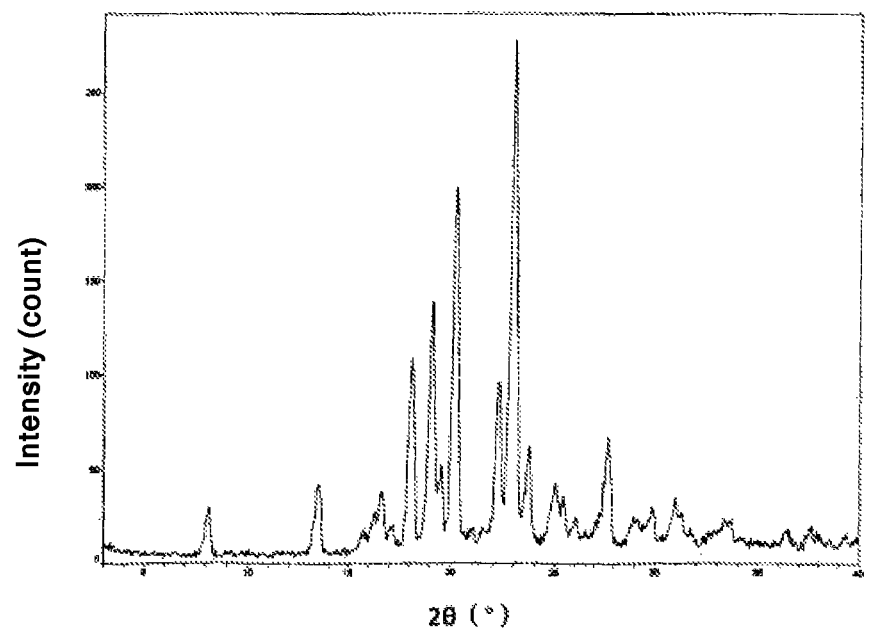
FIG. 1 is the XRPD spectrum of a crystal form I prepared in embodiment 2.

The XRPD spectrum thereof is shown in FIG. 1.

Figure 2:
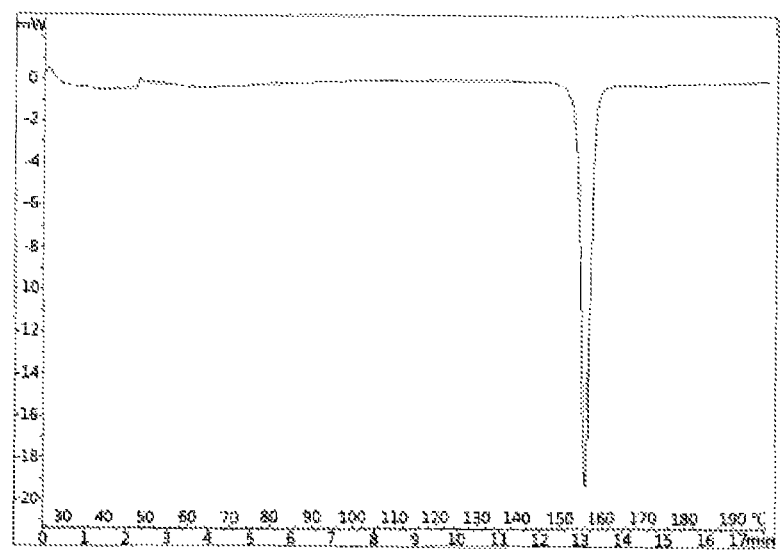
FIG. 2 is the DSC spectrum of the crystal form I prepared in embodiment 2.

The DSC spectrum is shown in FIG. 2. Display: the melting point is 154.8° C.

Figure 3:
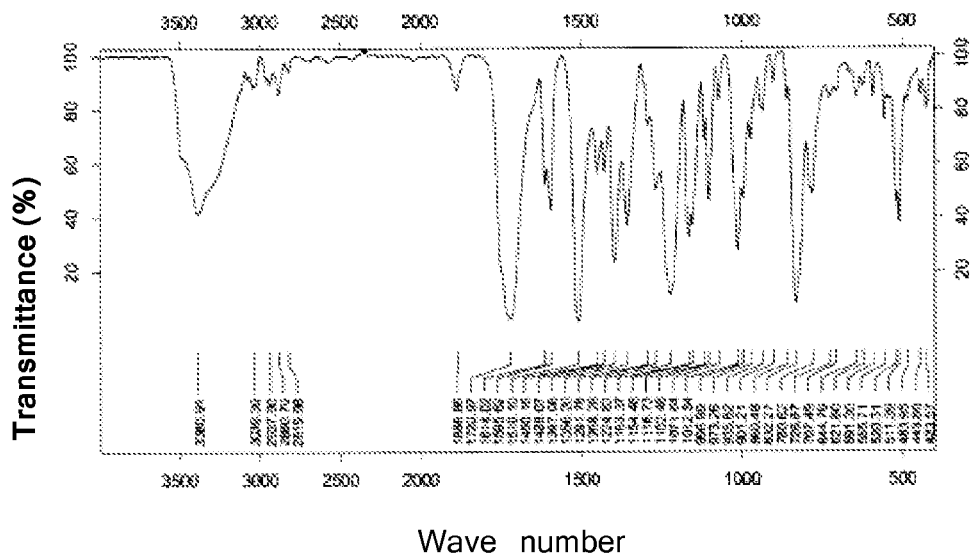
FIG. 3 is the IR spectrum of the crystal form I prepared in embodiment 2.

The infrared spectrum is shown in FIG. 3.

Embodiment 3

Preparation of Crystal Form I

The operating process is identical to that of the embodiment 2, excepting respectively replacing the methanol with tetrahydrofuran, iso-propanol, acetone, n-propanol, acetic acid, n-butylalcohol, ethyl acetate, acetonitrile and N,N-dimethylformamide to respectively obtain the crystal form I. The XRPD spectrum of the obtained crystal form I is identical to the XRPD spectrum of the crystal form I prepared in embodiment 2.

Embodiment 4

Preparation of Crystal Form I

Add 1 g of the compound of formula A into 1 mL of ethanol, completely dissolve at the normal temperature, then add 10 mL of distilled water thereinto all at once, separate out a solid, filter the solid out, and dry at the normal temperature and pressure, wherein the obtained solid is the crystal form I. The output is 0.88 g, and the yield is 88%. The XRPD spectrum of the obtained crystal form I is identical to the XRPD spectrum of the crystal form I prepared in embodiment 2.

Embodiment 5

Preparation of Crystal Form I

Add 1 g of the compound of formula A into 1 mL of ethanol, warmly dissolve, then add 1.5 mL of distilled water thereinto at the normal temperature, crystallize solids out, filtrating the solids out, and drying the solids (the drying temperature is 35-40° C.), wherein the obtained solids are the crystals in form I. The output is 0.91 g, and the yield is 91%. The XRPD spectrum of the obtained crystal form I is identical to the XRPD spectrum of the crystal form I prepared in embodiment 2.

Embodiment 6

Preparation of Crystal Form I

Add 1 g of the compound of formula A into a 10 mL crystallizer, add 2 mL of ethyl acetate thereinto, stir at the room temperature till complete dissolving, dropwise add 2 mL of n-heptane thereinto to crystallize out a large amount of solids, filtrate the solids out, then perform vacuum drying (the drying temperature is 35-40° C.), wherein the dried solids are namely the crystal form I. The output is 0.75 g, and the yield is 75%. The XRPD spectrum of the obtained crystal form I is identical to the XRPD spectrum of the crystal form I prepared in embodiment 2.

Embodiment 7

Preparation of Crystal Form I

Figure 13:
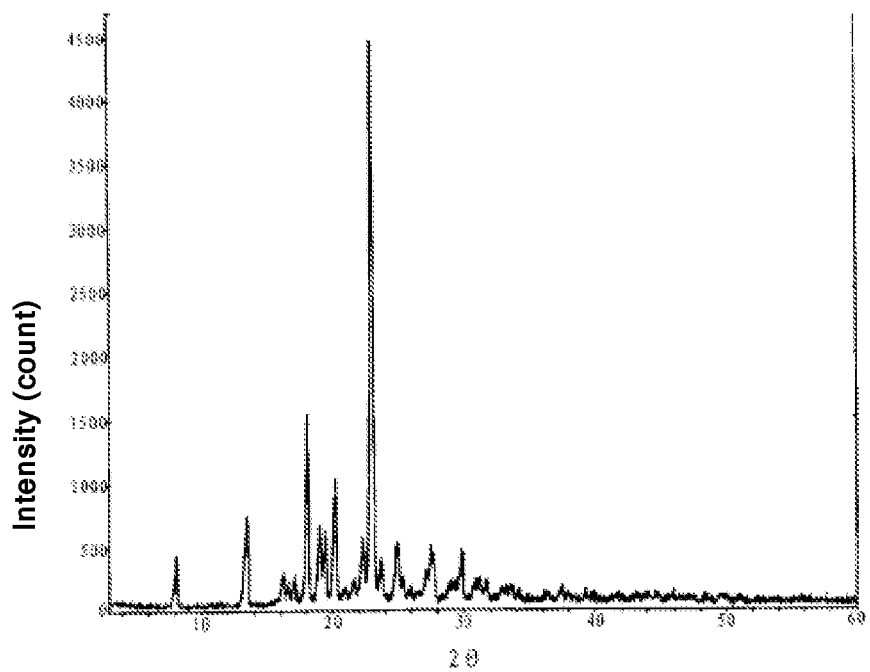
FIG. 13 is the XRPD spectrum of a crystal form I prepared in embodiment 7.

Add 1 g of the compound of formula A into 5 mL of methylene chloride, completely dissolve under heating and refluxing conditions, then slowly cool the solution to the normal temperature, crystallize out solids, filtrate the solids out, and dry them at the normal temperature and pressure, wherein the dried solids are namely the crystal form I. The output is 0.68 g, and the yield is 68%. The XRPD spectrum thereof is shown in FIG. 13.

Embodiment 8

Preparation of Crystal Form I

Figure 14:
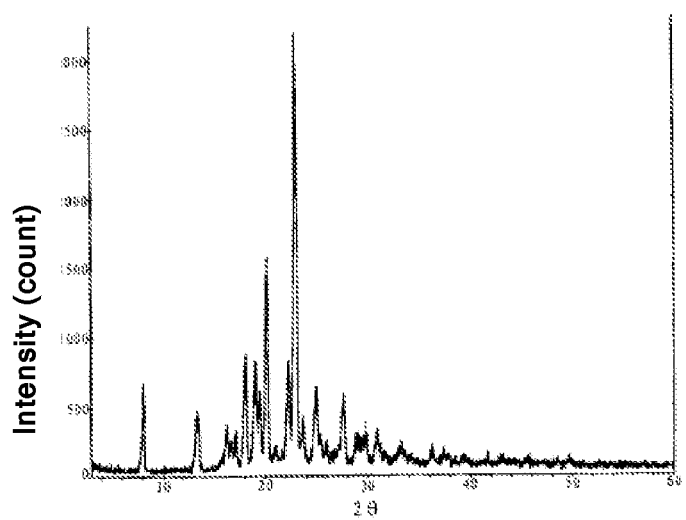
FIG. 14 is the XRPD spectrum of a crystal form I prepared in embodiment 8.

Add 1 g of the compound of formula A into 10 mL of toluene, completely dissolve under heating and refluxing conditions, then slowly cool to the normal temperature, crystallize out solids, filtrate the solids out, and dry them at the normal temperature and the normal pressure, wherein the dried solids are namely the crystal form I. The output is 0.77 g, and the yield is 77%. The XRPD spectrum thereof is shown in FIG. 14.

Embodiment 9

Preparation of Crystal Form II

Add 0.7 g of the compound of formula A into a 18 mL crystallizer, then add 1.7 mL of ethanol thereinto, completely dissolve at 50° C., then add 1 mL of purified water thereinto, stop heating, cool naturally, volatilize the solvent, at the normal temperature and the normal pressure, and filtrate after a large amount of acicular crystals are crystallized out naturally. Place the solids at the normal temperature for drying around 24 h, thus obtaining the crystal form II, wherein the output is 0.54 g, and the yield is 77%.

The XRPD spectrum thereof is shown in FIG. 4.

Figure 5:
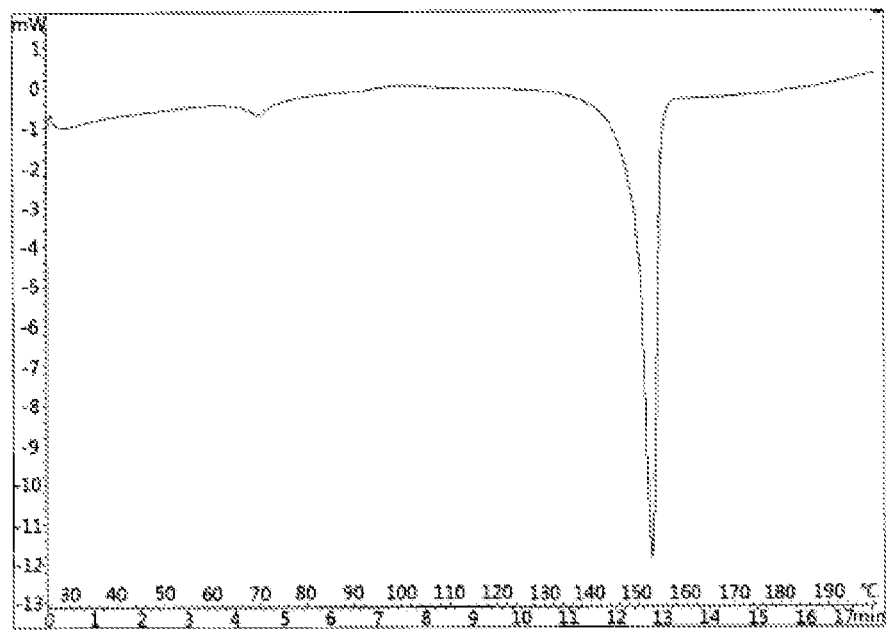
FIG. 5 is the DSC spectrum of the crystal form II prepared in embodiment 9.

The DSC spectrum is shown in FIG. 5. Display: the melting point is 152.14° C.

Figure 6:
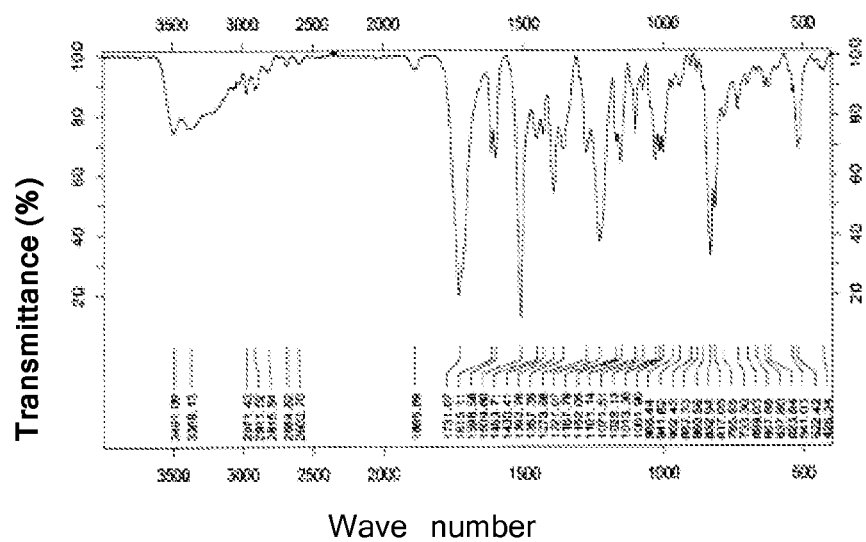
FIG. 6 is the IR spectrum of the crystal form II prepared in embodiment 9.

The infrared spectrum is shown in FIG. 6.

Embodiment 10

Preparation of Crystal Form II

Add 0.7 g of the compound of formula A into a 18 mL crystallizer, then add 1.7 mL of iso-propanol thereinto, completely dissolve at 50° C., then add 1 mL of purified water thereinto, stop heating, cool naturally, volatilize the solvent, at the normal temperature and the normal pressure, and filtrate after a large amount of acicular crystals are crystallized out naturally. Place the solids at the normal temperature for drying around 24 h, thus obtaining the crystal form II, wherein the output is 0.60 g, and the yield is 85%. The XRPD spectrum of the obtained crystal form II is identical to the XRPD spectrum of the crystal form II prepared in embodiment 9.

Embodiment 11

Preparation of Crystal Form II

Add 1 g of the compound of formula A into 10 mL of ethanol, completely dissolve at the normal temperature, then add 1 mL of distilled water thereinto, and volatilize the solvent at the normal temperature and the normal pressure. After the solvent is volatilized completely, the solids obtained are the crystals in form II. The XRPD spectrum of the obtained crystal form II is identical to the XRPD spectrum of the crystal form II prepared in embodiment 9.

Embodiment 12

Preparation of Crystal Form II

Weigh 1 g of the compound of formula A and add into a crystallizer, add 5 mL of anhydrous ethanol to stir, vibrate, and dissolve clearly, then add 1 mL of distilled water, wherein white casse is generated at the bottom of the flask. Shake the crystallizer until the casse disappears. Open the cover of the crystallizer to let the solvent volatilize naturally, thus obtaining the crystal form II. The XRPD spectrum of the obtained crystal form II is identical to the XRPD spectrum of the crystal form II prepared in embodiment 9.

Embodiment 13

Preparation of Crystal Form III

Add 0.4 g of the compound of formula A into the mixed solvent of 4 mL of tert-butyl alcohol and 0.3 mL of ethanol, completely dissolve at the normal temperature, then add mL of distilled water thereinto, crystallize out solids, filtrate the solid out, and dry at the normal temperature and the normal pressure, wherein the obtained solids are the crystals in form III. The output is 0.3 g, and the yield is 75%.

The XRPD spectrum thereof is shown in FIG. 7.

Figure 8:
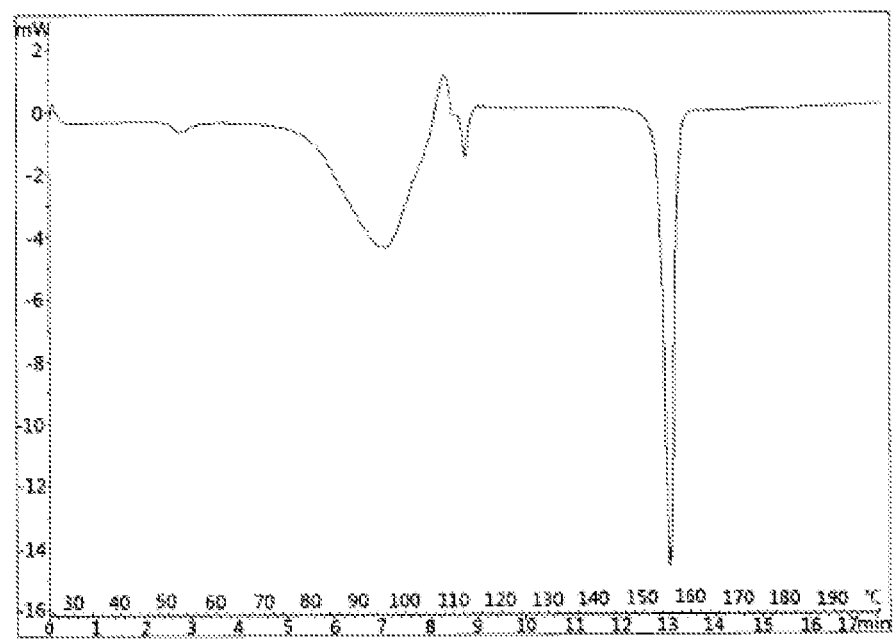
FIG. 8 is the DSC spectrum of the crystal form III prepared in embodiment 13.

The DSC spectrum is shown in FIG. 8. Display: the temperatures corresponding to three heat absorption peaks are respectively 105.94° C., 112.53° C., and 157.11° C.

Figure 9:
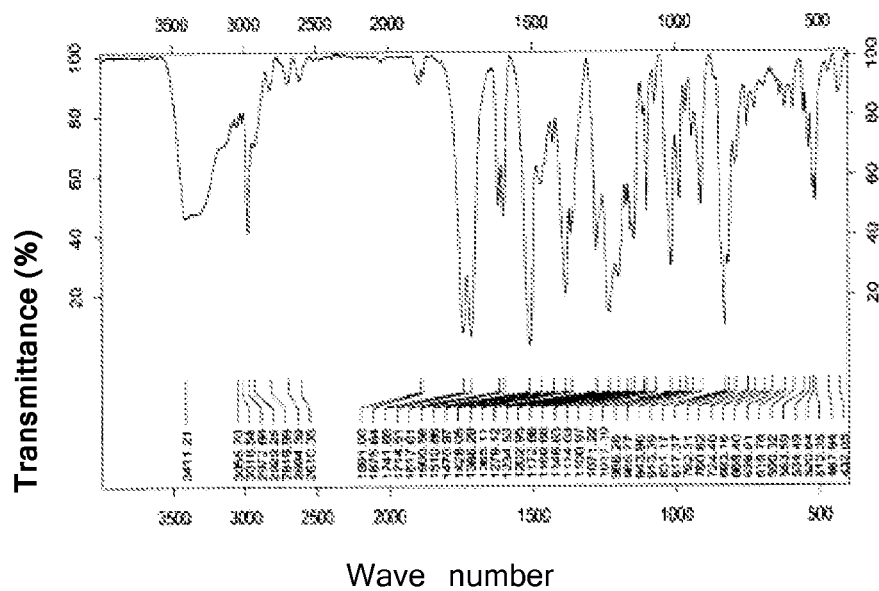
FIG. 9 is the IR spectrum of the crystal form III prepared in embodiment 13.

The infrared spectrum is shown in FIG. 9.

Embodiment 14

Preparation of Crystal Form III

Add 0.2 g of the compound of formula A and 2 mL of tert-butyl alcohol into a 20 mL crystallizer, stir, heat to 50° C., add 0.4 mL of ethanol, dissolve clearly, add 5 mL of distilled water all at once under the condition of 50° C., wherein a large amount of white solids crystallized out immediately. Pour the solid suspension from the crystallizer into a culture dish, and volatilize naturally, wherein the volatilizing time is no less than 24 h, thus obtaining the crystal form III. The XRPD spectrum of the obtained crystal form III is identical to the XRPD spectrum of the crystal form III prepared in embodiment 13.

Embodiment 15

Preparation of Crystal Form III

Add 1 g of the compound of formula A into a 25 mL crystallizer, then add 15 mL of tert-butyl alcohol thereinto, dissolve sufficiently at 50° C., then naturally cool to the room temperature, wherein solids are crystallized out. Filtrate the solid and dry at the normal temperature and the normal pressure, wherein the obtained solids are the crystals in form III. The output is 0.89 g, and the yield is 89%. The XRPD spectrum of the obtained crystal form III is identical to the XRPD spectrum of the crystal form III prepared in embodiment 13.

Embodiment 16

Preparation of the Amorphous Form

Add 1.0 g of the compound of formula A into a 18 mL crystallizer, then add 1 mL of ethanol thereinto, and dissolve sufficiently at 50° C. After the dissolving is completed, cool it to the room temperature, quickly add 5 mL of n-hexane thereinto under a quick stirring state to obtain vaporous slurry, take the suspended solids out, and lyophilize the solids for 1 hour, wherein an obtained white solids are in the amorphous form. The output is 0.92 g, and the yield is 92%.

The XRPD spectrum thereof is shown in FIG. 10.

Figure 11:
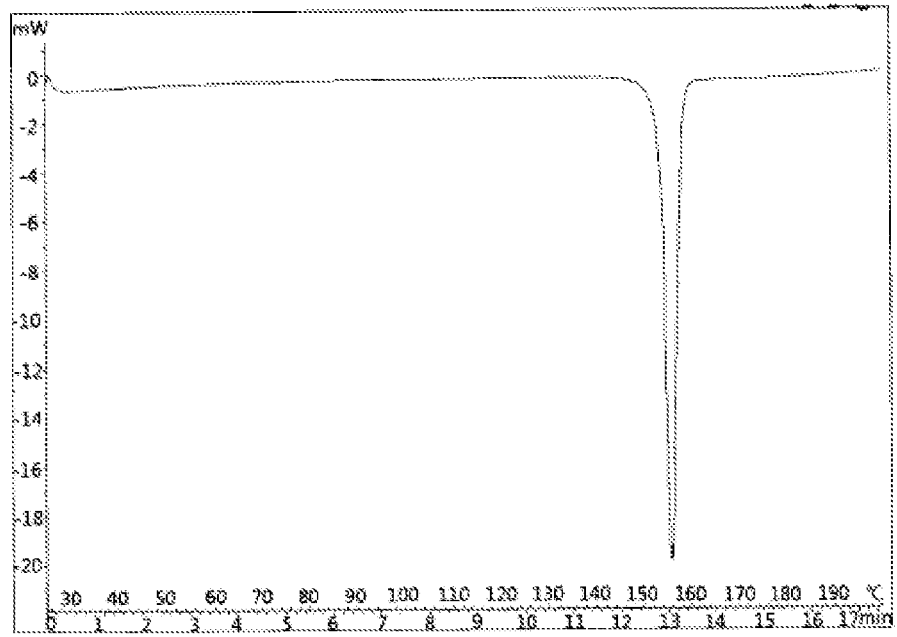
FIG. 11 is the DSC spectrum of the amorphous form prepared in embodiment 16.

The DSC spectrum is shown in FIG. 11.

Figure 12:
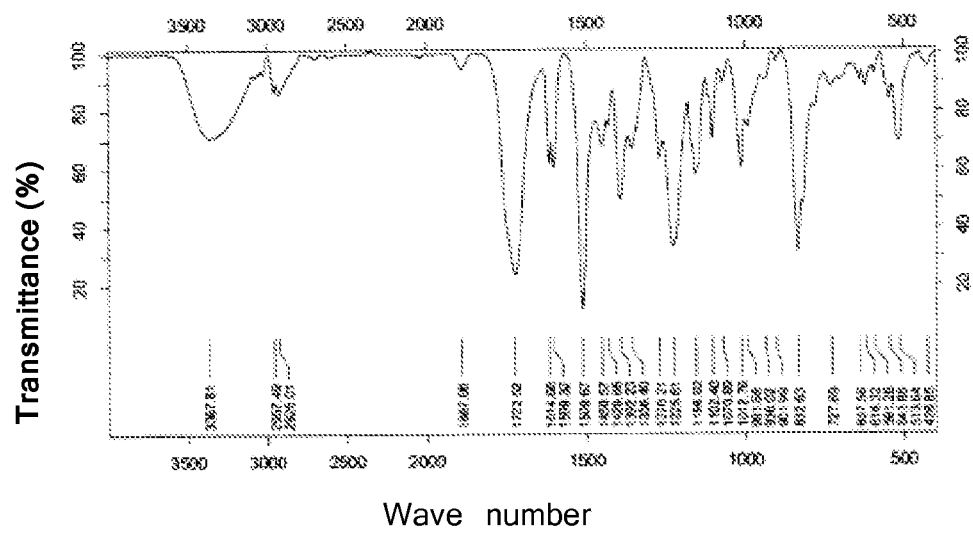
FIG. 12 is the IR spectrum of the amorphous form prepared in embodiment 16.

The infrared spectrum is shown in FIG. 12.

Embodiment 17

Preparation of the Amorphous Form

Add 1.0 g of the compound of formula A into a 18 mL crystallizer, then add 1 mL of propanol thereinto, and dissolve sufficiently at 50° C. After the dissolving is completed, cool the solution to the room temperature, quickly add 5 mL of n-pentane thereinto under a quick stirring state to obtain a vaporous suspension, take the slurry out, and lyophilize the slurry for 1 hour, wherein the obtained white solids are in the amorphous form. The output is 0.96 g, and the yield is 96%. The XRPD spectrum of the obtained amorphous form is identical to the XRPD spectrum of the amorphous form prepared in embodiment 16.

Embodiment 18

Preparation of the Amorphous Form

Completely dissolve 1 g of the compound of formula A into 1 mL of ethanol at the normal temperature, then add 5 mL of n-hexane thereinto, mix sufficiently, and then lyophilize the slurry (placing a cold source at the temperature of −51° C. with the degree of vacuum of 208 Pa) for 40 min, wherein an obtained solids are namely in the amorphous form. The XRPD spectrum of the obtained amorphous form is identical to the XRPD spectrum of the amorphous form prepared in embodiment 16.

Embodiment 19

Preparation of the Amorphous Form

Weigh 1 g of the compound of formula A and put into a crystallizer, add 1 mL of anhydrous ethanol to stir, heat up to 50° C., dissolve clearly in 1 min, dropwise add two drops of DMF, then pour the suspension into a culture dish, add 5 mL of n-hexane, and shake evenly, then white casse is produced. Put the culture dish into a lyophilizer for lyophilizing, take the culture dish out, thus obtaining the amorphous form. The XRPD spectrum of the obtained amorphous form is identical to the XRPD spectrum of the amorphous form prepared in embodiment 16.

Stability Test Data

1. Long Term Stability Test

In accordance with the stability test guiding principles (Chinese Pharmacopoeia 2010 Edition 2—Annex XIX C), prepare the samples of the crystal form I of the compound of formula A described in embodiment 6 in a commercial package, place the samples in a thermotank at the temperature of 25° C.±2° C. with the relative humidity of 60%±10%, take each sample from the samples once at the ends of the third month, the sixth month and the ninth month respectively to detect the key stability inspection items of each sample and compare with the result of the sample at the zero day, wherein see Table 3 for the comparisons.

TABLE 3

| | | Long term stability test results | | | |
|---|---|---|---|---|---|
| Inspection item | Limitation requirements | Time (month) | | | |
| | | 0 | 3 | 6 | 9 |
| Character | White or off-white crystalline powder | Off-white crystalline powder | Off-white crystalline powder | Off-white crystalline powder | Off-white crystalline powder |
| X-diffraction | Crystalline powder, consistent with that of zero month | Having crystalline | Consistent with that of zero month | Consistent with that of zero month | Consistent with that of zero month |
| Melting point | 149-153° C. | 149.8-152.1° C. | 149.5-151.6° C. | 149.3-151.2° C. | 149.7-152.0° C. |
| Relevant substances | Diastereomer shall not exceed 1.0% | Not detected | Not detected | Not detected | Not detected |
| | Single maximum unknown foreign matter shall not exceed 0.3% | 0.097 | 0.1013 | 0.0956 | 0.0940 |
| | Total foreign matter shall not exceed 1.5% | 0.342 | 0.3488 | 0.3551 | 0.3581 |
| Isomer | E-isomer shall not exceed 0.5% | / | / | / | 0.0161 |
| | Enantiomer shall not exceed 0.5% | / | / | / | 0.0587 |
| Moisture | Moisture shall not exceed 2.0% | 0.23 | 0.41 | 0.56 | 0.32 |
| Content | Based on anhydride, the content of $C_{25}H_{21}F_2NO_3$ shall be no less than 97.0% | 98.74 | 98.99 | 98.83 | 98.91 |

Conclusion: after the stability test of nine month long term, various inspection indexes of the samples do not change apparently and all meet the specifications.

2. Accelerated Stability Test

In accordance with the stability test guiding principles (Chinese Pharmacopoeia 2010 Edition 2—Annex XIX C), prepare the sample of the crystal form I of the compound of formula A described in embodiment 6 in a commercial package, place the samples in a thermotank at the temperature of 40° C.±2° C. with the relative humidity of 75%±5%, with the duration of 6 months, take each sample once at the ends of the first month, the second month, the third month and the sixth month respectively to detect the key stability inspection items and compare with the results of the sample at the zero day, wherein see Table 4 for the comparisons.

TABLE 4

Accelerated stability test results

| Inspection item | Limitation requirements | Time (month) | | | | |
|---|---|---|---|---|---|---|
| | | 0 | 1 | 2 | 3 | 6 |
| Character | White or off-white crystalline powder | Off-white crystalline powder | Off-white crystalline powder | Off-white crystalline powder | Off-white crystalline powder | Off-white crystalline powder |
| X-diffraction | Crystalline powder, consistent with that of zero month | Having crystalline | / | / | Consistent with that of zero month | Consistent with that of zero month |
| Melting point | 149-153° C. | 149.8-152.1° C. | 149.3-151.5° C. | 149.7-152.1° C. | 149.7-152.1° C. | 149.5-151.9° C. |
| Relevant substances | Diastereomer shall not exceed 1.0% | Not detected | 0.0128 | Not detected | Not detected | Not detected |
| | Single maximum unknown foreign matter shall not exceed 0.3% | 0.097 | 0.1004 | 0.0856 | 0.0983 | 0.2017 |
| | Total foreign matter shall not exceed 1.5% | 0.342 | 0.3757 | 0.3650 | 0.3717 | 1.0828 |
| Moisture | Moisture shall not exceed 2.0% | 0.20 | 0.30 | 0.28 | 0.37 | 0.44 |
| Content | Based on anhydride, the content of $C_{25}H_{21}F_2NO_3$ shall be no less than 97.0% | 98.71 | 99.11 | 98.82 | 98.78 | 97.97 |

Conclusion: the accelerated stability test results indicate that the relevant substances are grown significantly in the sixth month and the content is reduced at a certain level; however, both of the two are within the acceptable range, and other indexes are substantially not changed apparently.

Those skilled in the art can understand that some modifications or alternations may be made to the present invention under the teaching of this specification. These modifications and alternations shall also fall within the scope defined in the claims of the present invention.

The invention claimed is:

1. A crystal form I of the compound of formula A structured as follows,

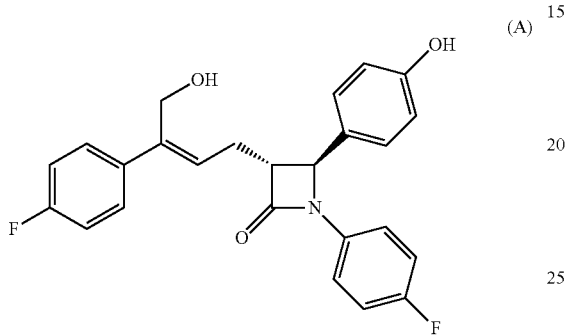

wherein an X-ray powder diffraction spectrum radiated by Cu-Kα and characterized in degrees 2θ has following characteristic peaks at 8.17±0.20°, 13.53±0.20°, 16.67±0.20°, 18.13±0.20°, 19.14±0.20°, 19.57±0.20°, 20.26±0.20°, 22.32±0.20°, 23.05±0.20°, 23.77±0.20°, 25.03±0.20°, 27.69±0.20° and 30.99±0.20°.

2. The crystal form I according to claim 1, wherein the X-ray powder diffraction spectrum characterized in degrees 2θ further has following characteristic peaks at 15.76±0.20°, 16.25±0.20°, 17.14±0.20°, 21.12±0.20°, 25.50±0.20°, 26.02±0.20°, 28.95±0.20°, 29.84±0.20°, 33.34±0.20°, 36.32±0.20° and 37.57±0.20°.

3. A preparation method of the crystal form I of the compound of formula A according to claim 1, wherein the preparation method is selected from any one of the following methods:

method (1), comprising the following steps of:
1) dissolving the compound of formula A into an organic solvent to prepare a saturated solution, wherein the organic solvent is selected from $C_1$-$C_4$ linear alcohol, acetonitrile, furans, carboxylic acid, ester, amide or ketone;
2) adding water or $C_2$-$C_8$ ether anti-solvent in an amount that is more than the volume of the organic solvent in step 1) into the foregoing saturated solution all in once to crystallize out the solids of the crystal form I; and
3) collecting the obtained solids, thus obtaining the crystals in form I;

method (2), comprising the following steps of:
1) dissolving the compound of formula A into $C_{1-6}$ alkyl $C_{1-6}$ carboxylate to obtain a solution, wherein the ratio of the mass of the compound of formula A in grams to the volume of the $C_{1-6}$ alkyl $C_{1-6}$ carboxylate in mL is 1:1.5-5;
2) adding $C_6$-$C_7$ alkane anti-solvent dropwise in an amount that is 1 to 3 times the volume of the $C_{1-6}$ alkyl $C_{1-6}$ carboxylate in step 1) into the foregoing solution to crystallized out solids in the crystal form I; and
3) collecting the obtained solids, thus obtaining the crystals in form I;

method (3), comprising the following steps of:
adding the compound of formula A in grams into methylene chloride in mL wherein the weight:volume ratio of the compound of formula A to methylene chloride is 1:5, completely dissolving under heating and refluxing conditions, then slowly cooling to the normal temperature, separating out solids, filtrating, and drying at the normal temperature and the normal pressure, wherein the dried solids are namely the crystal form I; and method (4), comprising the following steps of:
adding the compound of formula A in grams into toluene in mL wherein the weight:volume ratio of the compound of formula A to toluene is 1:10, completely dissolving under heating and refluxing conditions, then slowly cooling to the normal temperature, crystallizing out solids, filtrating, and drying at the normal temperature and the normal pressure, wherein the dried solids are namely the crystal form I.

4. The preparation method according to claim 3, wherein the organic solvent in step 1) of the method (1) is selected from the group consisting of methanol, ethanol, n-propanol, iso-propanol, n-butylalcohol, tetrahydrofuran, acetic acid, ethyl acetate, acetonitrile, N,N-dimethylformamide and acetone.

5. The preparation method according to claim 3, wherein the volume of the water or $C_2$-$C_8$ ether anti-solvent added in step 2) of the method (1) is 1.5 to 10 times the volume of the organic solvent.

6. The preparation method according to claim 5, wherein the method (1) comprises the following steps of: dissolving the compound of formula A in grams into methanol in mL wherein the weight:volume ratio of the compound of formula A to methanol is 1:1 to prepare a saturated solution thereof under the normal temperature, then adding 10 times the amount of anti-solvent water in mL into the foregoing saturated solution all at once, filtrating solids that are crystallized out, placing the solids in a vacuum drying oven for drying, wherein the dried solids are namely the crystal form I.

7. The preparation method according to claim 3, wherein the $C_{1-6}$ alkyl $C_{1-6}$ carboxylate in step 1) of the method (2) is ethyl acetate.

8. The preparation method according to claim 3, wherein the $C_6$-$C_7$ alkane in step 2) of the method (2) is n-hexane or n-heptane.

9. The preparation method according to claim 8, wherein the method (2) comprises the following steps of: adding the compound of formula A in grams into a crystallizer, adding ethyl acetate in mL into the crystallizer wherein the weight:volume ratio of the compound of formula A to ethyl acetate is 1:2, stirring at room temperature till complete dissolving to obtain a solution, adding n-heptane in mL dropwise in an amount twice the amount of the compound of formula A into the foregoing solution to crystallize solids, then performing vacuum drying on the solids after the solids are filtrated out, wherein the dried solids are namely the crystal form I.

10. A pharmaceutical composition, comprising a therapeutically effective amount of the crystal form I according to claim 1.

11. A method for reducing plasma cholesterol contents, comprising the steps of administering to a sufferer in need the pharmaceutical composition according to claim 10.

12. The method according to claim 4, wherein the organic solvent in step 1) of the method (1) is selected from the group consisting of methanol and ethanol.

13. The method according to claim 5 where in the anti-solvent is water.

* * * * *